US010092635B2

(12) United States Patent
Vanden Bush et al.

(10) Patent No.: US 10,092,635 B2
(45) Date of Patent: *Oct. 9, 2018

(54) TUMOR VACCINES AND METHODS OF USE THEREOF (71) Applicant: UNIVERSITY OF IOWA RESEACH FOUNDATION, Iowa City, IA (US)

(72) Inventors: Tony Vanden Bush, Iowa City, IA (US); Gail Bishop, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/765,266

(22) PCT Filed: Jan. 30, 2014

(86) PCT No.: PCT/US2014/013884
§ 371 (c)(1),
(2) Date: Jul. 31, 2015

(87) PCT Pub. No.: WO2014/120941
PCT Pub. Date: Aug. 7, 2014

(65) Prior Publication Data
US 2015/0374809 A1 Dec. 31, 2015

Related U.S. Application Data (60) Provisional application No. 61/759,903, filed on Feb. 1, 2013.

(51) Int. Cl.
*A61K 39/00* (2006.01)
*A61K 39/39* (2006.01)
*A61K 45/06* (2006.01)
*A61K 39/13* (2006.01)
*C12N 7/00* (2006.01)

(52) U.S. Cl.
CPC .......... *A61K 39/0011* (2013.01); *A61K 39/39* (2013.01); *A61K 45/06* (2013.01); *C12N 7/00* (2013.01); *A61K 2039/5152* (2013.01); *A61K 2039/6031* (2013.01); *A61K 2039/6056* (2013.01); *C12N 2770/32634* (2013.01)

(58) Field of Classification Search
None
See application file for complete search history.

(56) References Cited

U.S. PATENT DOCUMENTS

| | | | | |
|---|---|---|---|---|
| 6,221,664 B1 * | 4/2001 | Wen | ........................ | A61K 39/00 424/189.1 |
| 6,403,104 B1 | 6/2002 | Berd | | |
| 2003/0225251 A1 * | 12/2003 | Sallberg | ................... | C07K 7/06 530/350 |
| 2012/0195926 A1 * | 8/2012 | Bishop | ................... | A61K 39/00 424/204.1 |
| 2013/0012922 A1 * | 1/2013 | Klinman | .......... | A61K 47/48092 604/522 |
| 2014/0134204 A1 * | 5/2014 | Bishop | ................... | A61K 39/13 424/186.1 |

FOREIGN PATENT DOCUMENTS

| | | | |
|---|---|---|---|
| WO | WO0057911 | 10/2000 | |
| WO | 2011041691 A1 | 4/2011 | |
| WO | WO2011041691 | 4/2011 | |
| WO | WO 2011109422 A2 * | 9/2011 | ....... A61K 47/48092 |
| WO | WO2012138774 | 10/2012 | |

OTHER PUBLICATIONS

Chow et al. (PNAS, 1982, 79:7518-7521).*

* cited by examiner

*Primary Examiner* — Julie Wu
(74) *Attorney, Agent, or Firm* — Matthew W. Coryell; Davis, Brown, Koehn, Shors & Roberts, P.C.

(57) ABSTRACT

The present invention provides a therapeutic agent comprising an antibody-recognition epitope (ARE) covalently bound to a tumor cell, wherein the ARE is bound to an antibody that is specific for the ARE, to form a tumor cell:ARE:antibody complex, and kits and methods of using these tumor cell:ARE:antibody complexes.

5 Claims, 3 Drawing Sheets

TUMOR VACCINES AND METHODS OF USE THEREOF

RELATED APPLICATION

This application claims priority to U.S. Provisional Patent Application No. 61/759,903, filed 1 Feb. 2013, the entirety of which is incorporated herein by reference.

SEQUENCE LISTING

The instant application contains a Sequence Listing which has been submitted electronically in ASCII format and is hereby incorporated by reference in its entirety. Said ASCII copy, created on Feb. 28, 2014, is named 17023_133WO1_SL.txt and is 1,024 bytes in size.

BACKGROUND OF THE INVENTION

The immune system is quite complex and includes many different pathways for an organism to fight infectious pathogens and cancer cells. In general, the immune system is viewed as being able to mount two arms of an adaptive response, a humoral immune response (HIR) and/or a cell-mediated immune response (CMI). The HIR involves the production and secretion of antibodies produced in the cells of the B lymphocyte lineage (B-cells). Secreted antibodies bind to antigens on the surfaces target cells. The antibody-bound antigens are then destroyed by various cells in the immune system. Humoral immunity also refers to antibody production and the accessory processes that accompany it. It also refers to the effector functions of antibody, which include pathogen and toxin neutralization, classical complement activation, and opsonin promotion of phagocytosis and pathogen elimination.

The second type of adaptive immune response is cell-mediated immunity (CMI). CMI is an immune response that does not involve antibodies or complement but instead involves the activation of various immune cells, such as macrophages, natural killer cells (NK), antigen-specific cytotoxic T-lymphocytes, and the release of various cytokines in response to an antigen. Cellular immunity can protect the body by activating antigen-specific T-lymphocytes. These cells induce apoptosis in body cells displaying epitopes of foreign antigen on their surface, such as virus-infected cells, cells infected with intracellular bacteria, and cancer cells displaying tumor antigens. T cells activate macrophages and natural killer cells, enabling them to destroy intracellular pathogens, and stimulating cells to secrete a variety of cytokines that influence the function of other cells involved in adaptive and innate immune responses. Cell-mediated immunity is directed primarily at microbes that survive in phagocytes and microbes that infect non-phagocytic cells. It is most effective in removing virus-infected cells, but also participates in defending against fungi, protozoans, cancers, and intracellular bacteria.

Traditionally, as defined by the World Health Organization, a vaccine is any preparation intended to produce immunity to a disease by stimulating the production of antibodies. Vaccines include, for example, suspensions of killed or attenuated microorganisms, or products or derivatives of microorganisms. The most common method of administering vaccines is by inoculation, but some are given by mouth or nasal spray.

Current cancer treatments can involve chemotherapy, radiation, radiosurgery, corticosteroids, antiangiogenic therapy, immunotherapy, and surgery. There is an on-going need for further effective cancer treatments.

SUMMARY OF THE INVENTION

The present invention provides a therapeutic agent comprising an antibody-recognition epitope (ARE) covalently bound to a tumor cell, wherein the ARE is bound by an antibody that is specific for the ARE, to form a tumor cell:ARE:antibody complex. AREs are also called "antibody recognition elements" or "antibody reactive epitopes". In certain embodiments, the ARE is a carbohydrate or a peptide. In certain embodiments, the peptide moiety is a peptide epitope of a childhood vaccine immunogen. In certain embodiments, the epitope is a mumps, measles, rubella, chickenpox, influenza, tetanus, Pertussis, hepatitis A, hepatitis B or polio epitope. In certain embodiments, the epitope is a VP-1 epitope of polio. In certain embodiments, the VP-1 epitope of polio of is about 11-28 amino acids in length (such as about 18-28 amino acids) comprising, consisting essentially of, or consisting of IPALTAVETGA (SEQ ID NO: 1), AHSKEIPALTAVETGATA (SEQ ID NO: 2) or ALTAVETGAT (SEQ ID NO: 3). In certain embodiments, the ARE is a carbohydrate moiety. In certain embodiments, the carbohydrate moiety is a blood-type antigen. In certain embodiments, the blood-type antigen is an A-antigen, B-antigen or Rh-antigen. In certain embodiments, the carbohydrate moiety is carbohydrate epitope of a childhood vaccine immunogen. In certain embodiments, the carbohydrate epitope is a *Haemophilus influenzae* or *Pneumococcus* epitope. In certain embodiments, the antigen is bound to the ARE by means of an alpha-Gal linkage. In certain embodiments, the antigen is bound to the ARE by means of linker molecule. In certain embodiments, the linker molecule is formaldehyde, gluteraldehyde, MBS (m-Maleimidobenzoyl-N-hydroxysuccinimide ester) and/or Sulfo-MBS.

In certain embodiments, the tumor cell is a cancer is selected from breast, ovary, cervix, uterus, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, gastric, kidney, stomach, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, lymphoma and leukemia. In certain embodiments, the tumor cell is a cell line tumor cell.

In certain embodiments, the antibody is a human antibody or a humanized antibody. As used herein, the term "antibody" includes scFv, humanized, fully human or chimeric antibodies, single-chain antibodies, diabodies, and antigen-binding fragments of antibodies (e.g., Fab fragments). In certain embodiments, the antibody is a human antibody or a humanized antibody. In certain embodiments, the antibody is a single-chain Fv or an scFv fragment.

The present invention also provides, in certain embodiments, a pharmaceutical composition which comprises a pharmaceutically acceptable carrier or diluent and, as an active ingredient, a therapeutic agent as described herein. In certain embodiments, the composition is formulated for oral administration or injection.

The present invention also provides, in certain embodiments, a therapeutic agent as described herein for use in a method of treatment of a human or animal body by therapy.

The present invention also provides, in certain embodiments, the use of a therapeutic agent as described herein in the manufacture of a medicament for treating a disease or disorder arising from abnormal cell growth, function or behavior. In certain embodiments, the disease or disorder is cancer. In certain embodiments, the cancer is selected from solid tumors of the colon, breast, brain, liver, ovarian, gastric, lung, and head and neck. In certain embodiments, the cancer is selected from glioblastoma, melanoma, prostate, endometrial, ovarian, breast, lung, head and neck, hepatocellular, and thyroid cancers. In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

The present invention also provides, in certain embodiments, a method of treating a disease or disorder arising from abnormal cell growth, function or behavior, which method comprises administering to a patient in need thereof a therapeutic agent as described herein. In certain embodiments, the disease or disorder is cancer. In certain embodiments, the cancer is selected from glioblastoma, melanoma, prostate, endometrial, ovarian, breast, lung, head and neck, hepatocellular, and thyroid cancers. In certain embodiments, the cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's lymphoma and leukemia.

The present invention also provides, in certain embodiments, a process for producing a pharmaceutical composition comprising combining a therapeutic agent as described herein with a pharmaceutically acceptable carrier.

The present invention also provides, in certain embodiments, a kit for treating cancer, comprising: (a) a first pharmaceutical composition comprising a therapeutic agent as described herein; and (b) instructions for use. In certain embodiments, the kit further comprises (c) a second pharmaceutical composition, wherein the second pharmaceutical composition comprises a second compound having anti-hyperproliferative activity. In certain embodiments, the kit further comprises instructions for the simultaneous, sequential or separate administration of the first and second pharmaceutical compositions to a patient in need thereof. In certain embodiments, the first and second pharmaceutical compositions are contained in separate containers. In certain embodiments, the first and second pharmaceutical compositions are contained in the same container.

The present invention also provides, in certain embodiments, a product comprising (a) a therapeutic agent or a composition as described herein; and (b) a compound having anti-hyperproliferative activity; for separate, simultaneous or sequential administration in the prophylactic or therapeutic treatment of cancer.

In certain embodiments, the method further comprises introducing a repeat dose of the composition described herein. In certain embodiments, the animal is a human.

The present invention also provides, in certain embodiments, a compound comprising the therapeutic agent described herein for the manufacture of a medicament useful for the treatment of an infectious agent or cancer in a mammal.

The present invention also provides, in certain embodiments, a method of making a conjugated tumor vaccine comprising: (a) conjugating an ARE to a tumor cell to form an ARE-coated tumor cell, (b) killing the ARE-coated tumor cell to form an inactivated cell, and (c) contacting inactivated cell with an antibody specific for the ARE to form a conjugated tumor vaccine. In certain embodiments, the tumor cell is an autologous tumor cell. In certain embodiments, the tumor cell is a cell from a tumor cell line.

DETAILED DESCRIPTION OF THE INVENTION

The development of technologies to increase the immunogenicity of vaccines is of major interest to health professionals, military personnel, and the general public. The ability to increase an antigen's immunogenicity improves current vaccines and enhances the development of new vaccines to reduce infection related morbidity and mortality. In addition to combating infectious diseases, advances in vaccine development benefits cancer patients and suffers of chemical dependence (e.g., vaccination against active chemicals such as cocaine) through immunotherapeutics and immunologic intervention respectively.

Successful immunization results in activation of adaptive immune cells including B lymphocytes (also called "B cells"). B cell activation induces clonal expansion and differentiation into long lived Ab producing cells (plasma cells) and memory B cells. Thus immunized individuals express soluble Abs and maintain memory B cells, each able to recognize particular Ags contained within the original vaccine.

ARE-Tumor Cell Conjugated Compounds

Figure 1:
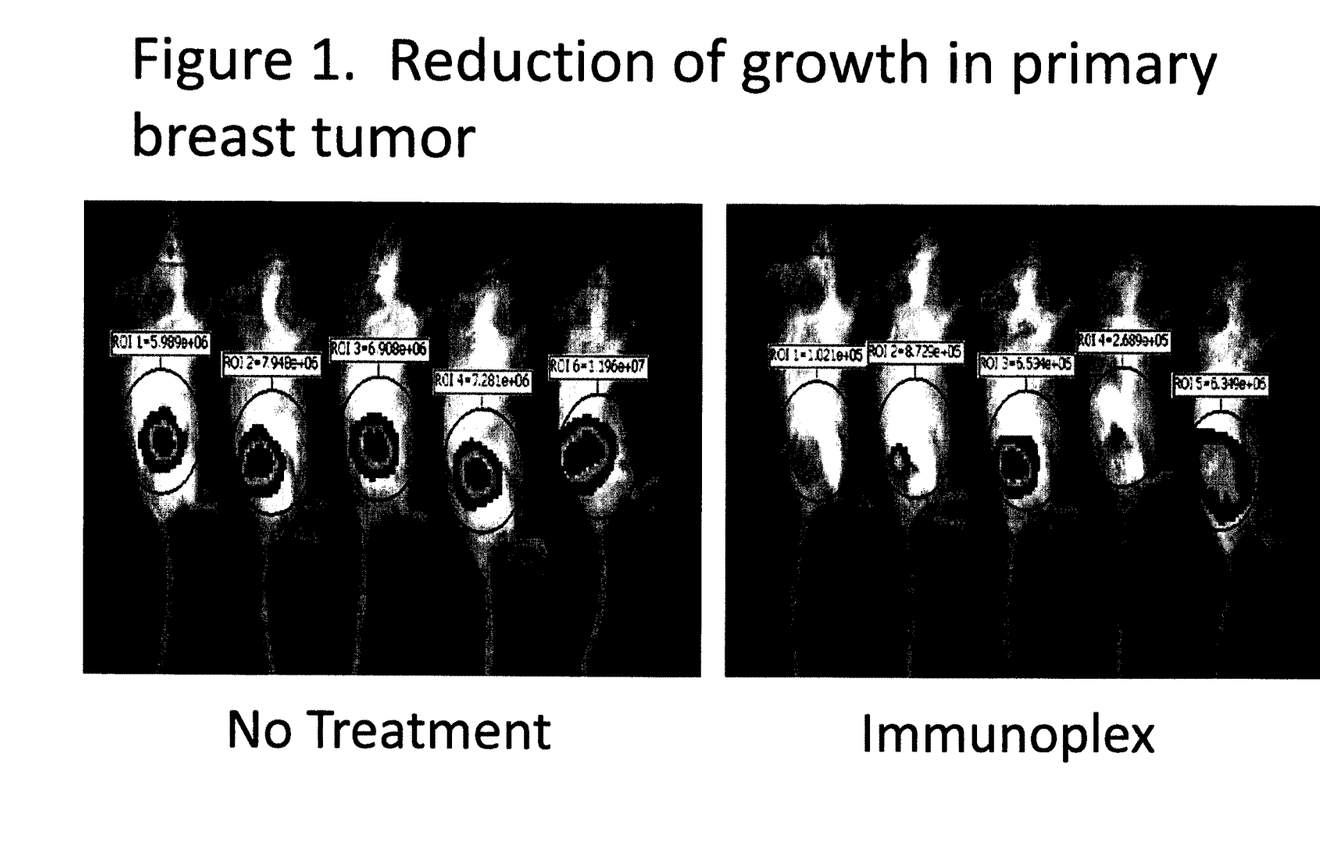
FIG. 1. Reduction of growth in primary breast tumors in vivo.
Figure 2:
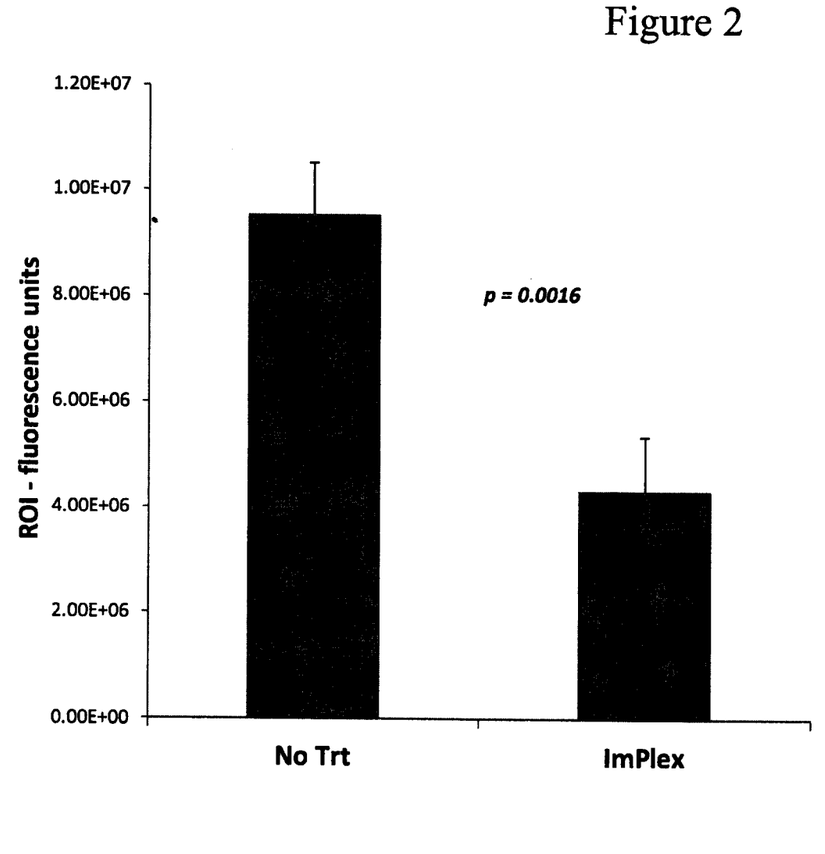
FIG. 2. Treatment of tumor bearing mice with immune complexed (IC) tumor cells. Tumor bearing mice were treated at day 6 post tumor challenge with Immune complexed (IC) tumor cells or not. At day 10 the relative tumor burden was analyzed by IVIS. The treatment with IC-tumor cells resulted in a decrease in tumor growth over the four day period. Data represented were pooled from two independent experiments. No Trt, n=15; ImPlex, n=10.
Figure 3:
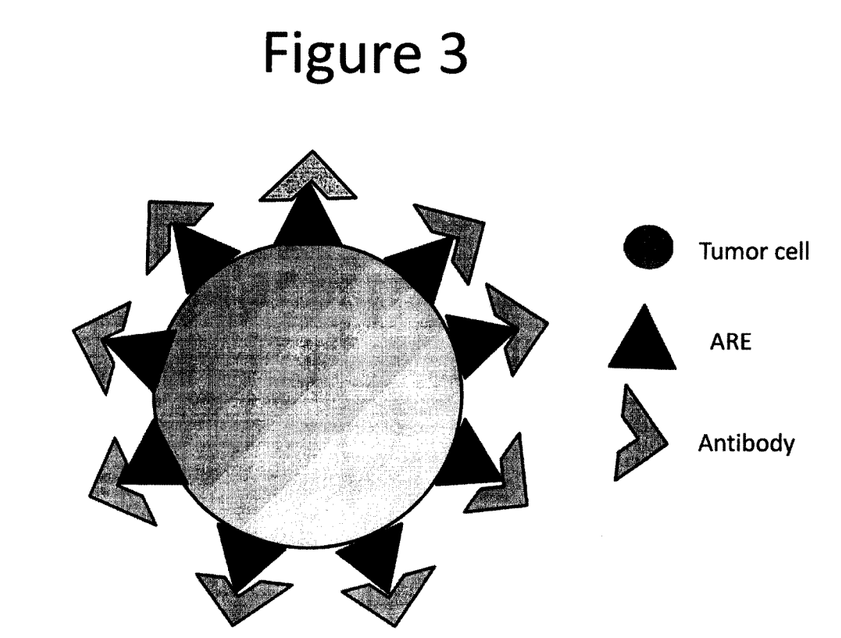
FIG. 3. Schematic diagram of one embodiment of the tumor cell:ARE:antibody complex.

The present invention provides compounds that are conjugates of AREs and tumor cells, which are operably linked either covalently or by means of a linker moiety, and are coated with an antibody that is specific for the ARE (FIG. 3).

A. Antibody Recognition Element (ARE)

An ARE (antibody recognition element) is a B cell epitope of any immunogen. To be used commercially, it is important that the ARE be recognized by a large pool of potential recipients. Therefore, AREs derived from commonly used recognition elements derived from prior vaccinations or naturally occurring infections for each recipient group are best.

In certain embodiments, the AREs of the present invention are peptides or carbohydrates. In one embodiment, the ARE is the VP-1 epitope of polio of about 11-28 amino acids in length comprising IPALTAVETGA (SEQ ID NO: 1). In another embodiment, the ARE is a variant of this HBsAg epitope containing an N-terminal addition of RAGG (SEQ ID NO:10) onto the amino acid sequence. In another embodiment, the ARE is a variant of the HBsAg epitope in that it contains other amino acids that are used as spacers or reactive groups. A further discussion of AREs is provided in WO 2011/041691 and WO 2012/138774, which are incorporated by reference herein.

B. Tumor Cells

The tumor cells that are linked to the AREs include a wide variety of tumor cells. In certain embodiments, the tumor cell is a cancer is selected from breast, ovary, cervix, uterus, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, gastric, kidney, stomach, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, lymphoma and leukemia. In certain embodiments, the tumor cell is a cell line tumor cell. In other embodiments, the tumor cell is an autologous tumor cell (i.e., isolated from the mammalian recipient).

As used herein, the tumor cells are isolated (e.g., from the patient or from a cell line) using standard methods, conjugated to the ARE, and then the cells are killed (or the cells can be killed first, and then conjugated to the ARE). In one embodiment, cells were suspended in isotonic buffer and irradiated (i.e., subjected to 5000 rads). In other embodiments, cells are killed using freeze/thaw cycles (e.g., 7 freeze thaw cycles using liquid nitrogen or other cooling method), UV treatment, or treating with chemical inducers of apoptosis.

C. Couplers/Linkers

ARE-tumor cell coupling is done either directly or using chemical linkers in accord with conventional practice.

In certain embodiments, the ARE and tumor cells are covalently linked using a chemical cross-linking agent. Many different cross-linking agents can be used. In certain embodiments the cross-linking agent is about 400-1000 daltons or about 3-12 angstroms in length. The cross-linkers useful in the present invention must be at least bivalent so that they can covalently join two molecules, the ARE to the antigen molecule. In certain embodiments, the cross-linker can be tris-succinimidyl aminotriacetate (TSAT); bis(sulfosuccinimidyl) suberate (BS3); disuccinimidyl suberate (DSS); bis(2-[sulfosuccinimidyooxycarbonloxy]ethylsulfone) (BOSCOES); bis(2-[succinimidyooxycarbonloxy]ethylsulfone) (Sulfo-BOSCOES); ethylene glycol bis-(succinimidylsuccinate) (EGS); ethylene glycol bis-(sulfosuccinimidylsuccinate) (Sulfo-EBS); or Dimethyl 3,3'-dithiobis-propionimidate (DTBP). In certain embodiments, the cross-linker is bivalent such as BS3, Sulfo-Boscoes, EGS, Sulfo-EBS, or DTBP.

Methods for attaching cross-linkers are well known in the art (c.f. Hermanson, 1995 Bioconjugate Techniques, Academic Press, Inc. New York, pp. 728; Wong, 1991 Chemistry of Protein Conjugation and Cross-linking. CRC Press, pp. 340; Brinkley, 1992 A brief survey of methods for preparing protein conjugates with dyes, haptens and cross-linking reagents Bioconjugate Chem. 3:2-13).

Examples of suitable linkers include formaldehyde, gluteraldehyde, MBS (m-Maleimidobenzoyl-N-hydroxysuccinimide ester) and/or Sulfo-MBS (the water soluble analog of MBS), etc. Examples of couplers/linkers are described in detail on the world-wide-web at solulink.com/white_papers/peptide and at piercenet.com and at piercenet.com/products/browse.cfm?fldID=020306.

D. Antibodies

The ARE-tumor cell complexes are coated with antibodies that specifically recognize the ARE on the surface of the tumor cells. As used herein, the term "antibody" refers to molecules capable of binding an epitope or antigenic determinant. As used herein the term "antibodies" includes monoclonal or polyclonal antibodies or an antibody fragments. This term includes whole antibodies and antigen-binding fragments thereof, including single-chain antibodies. In certain embodiments, the antibodies are human antigen binding antibody fragments and include, but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. The antibodies can be from any animal origin including birds (e.g. chicken) and mammals (e.g., human, murine, rabbit, goat, guinea pig, camel, horse and the like). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598.

Antibody specificity refers to the ability of an individual antibody combining site to react with only one antigenic determinant (i.e., the ARE in the present invention) or the ability of a population of antibody molecules to react with only one antigen. In the present invention, there is a high degree of specificity in antigen-antibody reactions, such that the anti-ARE antibodies do not significantly cross-react with other antigens. As used herein the term "binds specifically" means that the antibody binds to a target agent, e.g., the ARE, with a much higher degree of affinity than it binds to other antigens. In certain embodiments, the antibody binds to the target agent with a binding affinity of at least 2× greater than its affinity than to another antigen.

Linking of ARE to Tumor Cells and Coating of ARE-Tagged Tumor Cells

The present invention also provides, in certain embodiments, a method of making a conjugated tumor vaccine comprising: (a) conjugating an ARE to a tumor cell to form an ARE-coated tumor cell, (b) killing the ARE-coated tumor cell to form an inactivated cell, and (c) contacting irradiated cell with an antibody specific for the ARE to form a conjugated tumor vaccine. In certain embodiments, the tumor cell can be killed first, and then conjugated to the ARE. In certain embodiments, the ARE is conjugated directly to the tumor cell. In certain embodiments, the ARE is conjugated to the tumor cell by means of a linker. In certain embodiments, the killing is by irradiation, freeze/thaw cycling, UV treatment, and/or treating with chemical inducers of apoptosis.

In a certain embodiment, VP-1 ARE were chemically linked to the tumor cells and administered as an immune complex. In one example, the tumor cells were chemically linked to the VP-1 ARE, the cells were irradiated, and then mixed with an antibody that recognizes the ARE. The complex of ARE-tagged tumor cells+Antibody was then injected as a vaccine and compared to mice that did not receive any treatment. The result was a dramatic reduction in tumor growth, as indicated in Example 1 below.

Vaccines of the Invention

In certain embodiments, the present invention provides vaccines for use to protect mammals against or to treat cancer.

The term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes. As used herein "correspond essentially to" refers to an epitope that will elicit an immunological response at least substantially equivalent to the response generated by the native epitope. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest. Vaccines of the present invention can also include effective amounts of immunological adjuvants, known to enhance an immune response. An "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount." The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

The term "adjuvant" as used herein refers to non-specific stimulators of the immune response or substances that allow generation of a depot in the host, which when combined with the vaccine and pharmaceutical composition, respectively, of the present invention may provide for an even more enhanced immune response. Vaccines commonly contain two components: antigen (the therapeutic agent of the present invention) and adjuvant. The antigen is the molecular structure encoded by the pathogen or tumor against which the immune response is directed. To activate an antigen-specific immune response, the antigen must be presented in the appropriate immunostimulatory microenvironment. In certain embodiments, adjuvants establish such microenvironments by stimulating the production of immune-activating molecules such as proinflammatory cytokines. Vaccine efficacy depends on the types of antigen and adjuvant, and how they are administered. Striking the right balance among these components is key to eliciting the desired immunological result.

To immunize a subject, the composition is administered parenterally, usually by intramuscular or subcutaneous injection in an appropriate vehicle. Other modes of administration, however, such as oral, intranasal or intradermal delivery, are also acceptable.

Vaccine formulations will contain an effective amount of the active ingredient in a vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the biofilm peptide or fragment thereof in one or more doses. Multiple doses may be administered as is required to maintain a state of immunity to the bacterium of interest.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the purified composition can be isolated, lyophilized and stabilized. The composition may then be adjusted to an appropriate concentration, optionally combined with a suitable vaccine adjuvant, and packaged for use.

Definitions

"Bound" refers to binding or attachment that may be covalent, e.g., by chemically coupling, or non-covalent, e.g., ionic interactions, hydrophobic interactions, hydrogen bonds. Covalent bonds can be, for example, ester, ether, phosphoester, amide, peptide, imide, carbon-sulfur bonds, carbon-phosphorus bonds, and the like. The term "bound" is broader than and includes terms such as "conjugated," "coupled," "fused" and "attached."

The terms "protein," "peptide" and "polypeptide" are used interchangeably herein. The invention encompasses isolated or substantially purified protein compositions. In the context of the present invention, an "isolated" or "purified" polypeptide is a polypeptide that exists apart from its native environment and is therefore not a product of nature. A polypeptide may exist in a purified form or may exist in a non-native environment such as, for example, a transgenic host cell. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins encoded thereby are also encompassed by the present invention. By "fragment" or "portion" is meant a full length or less than full length of the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule.

"Wild-type" refers to the normal gene, or organism found in nature without any known mutation.

"Operably-linked" refers to the association of molecules so that the function of one is affected by the other.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to a reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

As used herein, the term "therapeutic agent" or "therapeutic complex" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

"Antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. An antigen can have one or more epitopes (B- and/or T-cell epitopes). Antigens as used herein may also be mixtures of several individual antigens. "Antigenic determinant" refers to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov). Polyclonal and monoclonal antibodies can be prepared by methods known to those skilled in the art. For example, the antibodies can be prepared by the methods described below.

An antigen prepared as described above is given to a mammal, such as a mouse, rat, hamster, guinea pig, horse, monkey, rabbit, goat, and sheep. This immunization can be performed by any existing method, including typically used intravenous injections, subcutaneous injections, and intraperitoneal injections. There are no restrictions as to the immunization intervals. Immunization may be carried out at intervals of several days to several weeks, preferably four to 21 days. A mouse can be immunized, for example, at a single dose of 10 to 100 µg (for example, 20 to 40 µg) of the antigen protein, but the dose is not limited to these values.

Before the first immunization, and three to seven days after the second and subsequent immunizations, blood is collected from the animals, and the sera are analyzed for antibody titer. To promote an immune response, an aggregating agent such as alum is preferably used. In general, selected mammalian antibodies have sufficiently high antigen binding affinity. Antibody affinity can be determined using a saturation binding assay, an enzyme-linked immunosorbent assay (ELISA), or a competitive assay (for example, radioimmunoassay).

Polyclonal antibodies can be screened by a conventional crosslinking analysis, such as that described in "Antibodies, A Laboratory Manual (Cold Spring Harbor Laboratories, Harlow and David Lane edit. (1988))." An alternative method is, for example, epitope mapping (Champe et al., J. Biol. Chem. 270:1388-1394 (1995)). A preferred method for determining polypeptide or antibody titers comprises quantifying antibody-binding affinity. In other embodiments, methods for assessing one or more biological properties of an antibody are also used in addition to or instead of the methods for determining antibody-binding affinity. Such analytical methods are particularly useful because they demonstrate the therapeutic effectiveness of antibodies. When an antibody exhibits an improved property in such analysis, its binding affinity is generally, but not always, enhanced.

Hybridomas that are used to prepare monoclonal antibodies can be obtained, for example, by the method of Milstein et al. (Kohler, G., and Milstein, C., Methods Enzymol. 1981, 73, 3-46). Myeloma cells to be fused with antibody-producing cells may be cell lines derived from any of the various animals, such as mice, rats, and humans, which are generally available to those skilled in the art. The cell lines to be used are drug-resistant, and cannot survive in a selective medium (e.g., HAT medium) in an unfused state, but can survive in a fused state. 8-azaguanine-resistant cell lines are generally used, which are deficient in hypoxanthine-guanine-phosphoribosyl transferase and cannot grow in a hypoxanthine-aminopterin-thymidine (HAT) medium. Myeloma cells include a variety of known cell lines, for example, P3x63Ag8.653 (J. Immunol. (1979) 123: 1548-1550), P3x63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), F0 (de St. Groth, S. F. et al., J. Immunol. Methods (1980) 35: 1-21), S194 (Trowbridge, I. S., J. Exp. Med. (1978) 148: 313-323), R210 (Galfre, G. et al., Nature (1979) 277: 131-133), and P3U1 (J. Exp. Med. 1979, 150:580; Curr Top Microbiol. Immunol. 1978, 81:1). Human myeloma and mouse-human heteromycloma cell lines can also be used to produce human monoclonal antibodies (Kozbar, J. Immunol. 133:3001 (1984); Brodeur et al., Monoclonal Antibody Production Techniques and Application, pp. 51-63 (Marcel Dekker, Inc., New York, 1987)). Antibody-producing cells are collected, for example, from animals sacrificed two to three days after the final immunization. Antibody-producing cells include spleen cells, lymph node cells, and peripheral blood cells. Spleen cells are generally used. Specifically, tissues such as spleens or lymph nodes are excised or collected from the various animals described above. Then, the tissues are crushed and the resulting material is suspended in a medium or buffer, such as PBS, DMEM, or RPMI1640, followed by filtration with a stainless mesh or the like. This is then centrifuged to obtain antibody-producing cells of interest.

The above-described myeloma cells and antibody-producing cells are then fused. Cell fusion is achieved by contacting the myeloma cells with the antibody-producing cells at a ratio of 1:1 to 1:20 in a medium for animal cell culture, such as MEM, DMEM, and RPMI-1640, at 30 to 37° C. for one to 15 minutes in the presence of a fusion-promoting agent. To promote cell fusion, the antibody-producing cells and the myeloma cells may be fused using a commercially available cell-fusion device, using a fusion-promoting agent, such as polyethylene glycol (mean molecular weight 1,000 to 6,000 (Da)) or polyvinyl alcohol, or a virus for fusion, such as Sendai virus.

Hybridomas of interest are selected from the cells after cell fusion. The selection methods include methods using selective propagation of cells in a selective medium. Specifically, a cell suspension is diluted with an appropriate medium, and then the cells are plated on to microtiter plates. An aliquot of selection medium (for example, HAT medium) is added to each well, and then the cells are cultured while the selection medium is appropriately exchanged. The cells grown as a result can be saved as hybridomas.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Methods for preparing monoclonal antibodies from the obtained hybridomas include standard cell culture methods and methods comprising ascites production. In cell culture methods, hybridomas are cultured for two to 14 days under standard culture conditions (for example, at 37° C. at 5% $CO_2$ atmosphere), in a culture medium for animal cells, such as RPMI-1640 or MEM containing 10 to 20% fetal calf serum, or serum-free medium, and antibodies are then prepared from the culture supernatant. In the method comprising ascites production, hybridomas are administered to the peritoneal cavities of mammalian individuals of the same species as that from which the myeloma cells are derived, and the hybridomas proliferate in to large quantities. Ascites or serum is then collected after one to four weeks. To enhance ascites production, for example, pristane (2,6,10, 14-tetramethylpentadecane) may be pre-administered to the peritoneal cavity.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

Methods for obtaining human antibodies are also known. For example, desired human antibodies with antigen-binding activity can be obtained by (1) sensitizing human lymphocytes with antigens of interest or cells expressing antigens of interest in vitro; and (2) fusing the sensitized lymphocytes with human myeloma cells such as U266 (see Examined Published Japanese Patent Application No. (JP-B) Hei 1-59878). Alternatively, the desired human antibody can also be obtained by using an antigen to immunize a transgenic (Tg) animal that comprises a partial or entire repertoire of human antibody genes (see Nature Genetics 7:13-21 (1994); Nature Genetics 15:146-156 (1997); Nature 368: 856-859 (1994); International Patent Application WO 93/12227, WO 92/03918, WO 94/02602, WO 94/25585, WO 96/34096, and WO 96/33735). Specifically, such Tg animals are created as follows: a nonhuman mammal in which the loci of heavy and light chains of an endogenous immunoglobulin have been disrupted, and instead, the loci of heavy and light chains of a human immunoglobulin have been introduced via Yeast artificial chromosome (YAC) vectors and the like, is obtained by creating knockout animals or Tg animals, or mating such animals. The immunoglobulin heavy chain loci can be functionally inactivated, for example, by introducing a defect at a certain site in a J region or C region (e.g., Cμ region). The immunoglobulin light chains (e.g., κ chain) can be functionally inactivated, for example, by introducing a defect at a certain site in a J region or C region, or a region comprising the J and C regions.

Such a humanized antibody can also be obtained from culture supernatant, by using genetic engineering technology to transform eukaryotic cells with cDNAs that encode each of the heavy and light chains of the antibody, or preferably vectors comprising these cDNAs, and then culturing the transformed cells that produce the recombinant human monoclonal antibody. The hosts are, for example, desired eukaryotic cells, preferably mammalian cells, such as CHO cells, lymphocytes, and myelomas.

Furthermore, techniques to obtain human antibodies by panning with a human antibody library are known. For example, the variable region of a human antibody is expressed as a single chain antibody (scFv) on the surface of a phage, using phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed, and then introduced into appropriate hosts and expressed to obtain human antibodies. Such methods are already well known (see WO 92/01047, WO 92/20791, WO 93/06213, WO 93/11236, WO 93/19172, WO 95/01438, and WO 95/15388).

When the antibody genes have been isolated and introduced into an appropriate host, hosts and expression vectors can be used in appropriate combination to produce the antibodies. As eukaryotic host cells, animal cells, plant cells, and fungal cells may be used. The animal cells include: (1) mammalian cells such as CHO, COS, myeloma, baby hamster kidney (BHK), HeLa, and Vero cells; (2) amphibian cells such as Xenopus oocytes; or (3) insect cells such as sf9, sf21, and Tn5, or silkworms. Known plant cells include cells derived from the *Nicotiana* genus such as *Nicotiana tabacum*, which can be callus cultured. Known fungal cells include yeasts such as the *Saccharomyces* genus, for example *Saccharomyces cerevisiae*, and filamentous fungi such as the *Aspergillus* genus, for example *Aspergillus niger*. Prokaryotic cells can also be used in production systems that utilize bacterial cells. Known bacterial cells include *E. coli* and *Bacillus subtilis*. The antibodies can be obtained by transferring the antibody genes of interest into these cells using transformation, and then culturing the transformed cells in vitro.

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., *Journal of Biochemical and Biophysical Methods* 24:107-117 (1992); Brennan et al., *Science* 229:81 (1985); Co, M. S. et al., *J. Immunol.*, 1994, 152, 2968-2976; Better, M. & Horwitz, A. H., *Methods in Enzymology*, 1989, 178, 476-496, Academic Press, Inc.; Plueckthun, A. & Skerra, A., *Methods in Enzymology*, 1989, 178, 476-496, Academic Press, Inc.; Lamoyi, E., *Methods in Enzymology*, 1989, 121, 663-669; Bird, R. E. et al., *TIBTECH*, 1991, 9, 132-137).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')$_2$. Other chemically crosslinked antibody fragments are also known to those skilled in the art. Pepsin digestion of an antibody yields two fragments; one is a F(ab')$_2$ fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')$_2$-SH fragments can be recovered directly from hosts, such as E. coli, and then allowed to form F(ab')$_2$ fragments by chemical crosslinking (Carter et al., Bio/Technology 10:163-167 (1992)). In an alternative method, F(ab')$_2$ fragments can be isolated directly from a culture of recombinant hosts.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., *J. Biomed. Mater. Res.* 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133,988).

An "immune response" refers to a humoral immune response and/or cellular immune response leading to the activation or proliferation of B- and/or T-lymphocytes and/ or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier. Preferably, antigen presenting cell may be activated.

A substance that "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}$Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In certain embodiments, the immune response in enhanced by a factor of at least about 2, such as by a factor of about 3 or more. The amount or type of cytokines secreted may also be altered. Alternatively, the amount of antibodies induced or their subclasses may be altered.

The terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

The term "immunotherapeutic" refers to a composition for the treatment of diseases, disorders or conditions. More specifically, the term is used to refer to a method of treatment wherein a beneficial immune response is generated by vaccination or by transfer of immune molecules. An "immunologically effective amount" refers to an amount of a composition sufficient to induce an immune response in an individual when introduced into that individual. In the context of active immunization, the term is synonymous with "immunogenically effective amount." The amount of a composition necessary to be immunologically effective varies according many factors including to the composition, the presence of other components in the composition, the antigen, the route of immunization, the individual, the prior immune or physiologic state etc.

Formulations and Methods of Administration

The vaccines and compositions of the invention may be formulated as pharmaceutical compositions and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Additional ingredients such as fragrances or antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In certain embodiments, the vaccine of the present invention reduces the size of the tumor in the subject by at least about 10%-100% (volume of tumor).

Example 1

Mice were given $1\times10^5$ 4 T-1 tumor cells on day 0. Six days post tumor induction, 4T-1 breast carcinoma cells from culture were disaggregated into a single cell suspension. The cells were repeatedly washed in PBS and resuspended to a final concentration of $2\times10^6$ cells/ml. Chemically active polio-ARE (ARE peptide reacted with Sulfo-MBS or other chemical protein crosslinker) was added to the 4T-1 cells at a concentration of 300 ug/ml. After 2 hours on ice, the cells were again washed in PBS and irradiated (5000 rads). The cells, now labeled with ARE, were incubated with monoclonal antibody against the ARE for 30 minutes on ice to form opsonized tumor cells (cells coated in antibody). A total of $2\times10^5$ cells were injected into mice subcutaneously, contralateral from the established 4T-1 tumor. Four days after treatment the mice were subjected to IVIS (in vitro imaging system) to analyze relative tumor burden between treated and non-treated mice. The results are provided in FIGS. 1 and 2.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms “a” and “an” and “the” and similar referents in the context of describing the invention are to be construed to cover both the singular and the plural, unless otherwise indicated herein or clearly contradicted by context. The terms “comprising,” “having,” “including,” and “containing” are to be construed as open-ended terms (i.e., meaning “including, but not limited to”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a disease or disorder arising from abnormal cell growth, function or behavior, which method comprises administering to a patient in need thereof a therapeutic agent comprising an antibody-recognition epitope (ARE) comprising an antibody-recognition epitope (ARE) comprising a VP-1 epitope of polio, chemically conjugated to a tumor cell, wherein the VP-1 epitope of polio of is about 18-28 amino acids in length and comprises IPALTAVETGA (SEQ ID NO: 1), AHSKEIPALTAVETGATA (SEQ ID NO: 2) or ALTAVETGAT (SEQ ID NO: 3), and wherein the ARE is bound to an antibody that is specific for the ARE, to form a tumor cell:ARE:antibody complex.

2. The method of claim 1 further comprising introducing a repeat dose of the composition.

3. The method of claim 1, wherein the ARE is a peptide moiety.

4. The method of claim 1, wherein the tumor cell is a killed tumor cell.

5. The method of claim 1, wherein the VP-1 epitope of polio consists of IPALTAVETGA (SEQ ID NO: 1), AHSKEIPALTAVETGATA (SEQ ID NO: 2) or ALTAVETGAT (SEQ ID NO: 3).

* * * * *

SEQUENCE LISTING

```
<160> NUMBER OF SEQ ID NOS: 4

<210> SEQ ID NO 1
<211> LENGTH: 11
<212> TYPE: PRT
<213> ORGANISM: Human poliovirus

<400> SEQUENCE: 1

Ile Pro Ala Leu Thr Ala Val Glu Thr Gly Ala
1               5                   10

<210> SEQ ID NO 2
<211> LENGTH: 18
<212> TYPE: PRT
<213> ORGANISM: Human poliovirus

<400> SEQUENCE: 2

Ala His Ser Lys Glu Ile Pro Ala Leu Thr Ala Val Glu Thr Gly Ala
1               5                   10                  15

Thr Ala

<210> SEQ ID NO 3
<211> LENGTH: 10
```

```
<212> TYPE: PRT
<213> ORGANISM: Human poliovirus

<400> SEQUENCE: 3

Ala Leu Thr Ala Val Glu Thr Gly Ala Thr
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Gly Gly
1
```